United States Patent [19]

Takahashi et al.

[11] 4,115,102

[45] Sep. 19, 1978

[54] PYRIDYL COMPOUND, HERBICIDAL COMPOSITION CONTAINING THE SAME AND METHOD OF USE THEREOF

[75] Inventors: Ryohei Takahashi, Kusatsu; Kanichi Fujikawa, Kyoto; Isao Yokomichi, Kusatsu; Yasuhiro Tsujii, Kusatsu; Nobuyuki Sakashita, Kusatsu, all of Japan

[73] Assignee: Ishihara Sangyo Kaisha, Ltd., Osaka, Japan

[21] Appl. No.: 805,387

[22] Filed: Jun. 10, 1977

Related U.S. Application Data

[62] Division of Ser. No. 623,517, Oct. 17, 1975, Pat. No. 4,046,553.

[30] Foreign Application Priority Data

Oct. 17, 1974 [JP] Japan .............................. 49-118676
Mar. 13, 1975 [JP] Japan .................................. 50-29556

[51] Int. Cl.$^2$ .................... C07D 213/64; A01N 9/22
[52] U.S. Cl. ................................... 71/94; 260/294.8 E
[58] Field of Search ...................... 260/294.8 E; 71/94

[56] References Cited

U.S. PATENT DOCUMENTS 3,151,024  9/1964  D'Amico et al. ............ 260/294.8 E

*Primary Examiner*—John M. Ford
*Attorney, Agent, or Firm*—Sughrue, Rothwell, Mion, Zinn and Macpeak

[57] ABSTRACT

α-[4-(5-Mono-substituted or 3,5-di-substituted-pyridyl-2-oxy)phenoxy]alkanecarboxylic acids and derivatives thereof useful as a herbicide; a herbicidal composition containing the compound; methods of controlling weeds using such materials and production of such materials.

8 Claims, No Drawings

PYRIDYL COMPOUND, HERBICIDAL COMPOSITION CONTAINING THE SAME AND METHOD OF USE THEREOF

This is a Division of application Ser. No. 623,517, filed Oct. 17, 1975 now U.S. Pat. No. 4,046,553, issued Sept. 6, 1977;

BACKGROUND OF THE INVENTION

1. Field of the Invention

This invention relates to a novel compound useful as a herbicide for agriculture and horticulture, to a herbicidal composition containing the same, and to methods of controlling weeds and the production thereof.

2. Description of the Prior Art

In recent years, a number of herbicides have been developed and put into practical use. These herbicides have contributed to a saving of labor and increased agricultural production. However, there is still room for improvement, and novel chemicals which have reduced effects on useful cultivated plants but have a strong herbicidal action on undesirable plants and which are very safe in regard to environmental pollution have been desired. For example, phenoxyalkanecarboxylic acids represented by 2,4-dichlorophenoxyacetic acid, which have been known for a long time, have superior controlling effects on broad-leafed weeds and find widespread use. However, since phenoxyalkanecarboxylic acids have only a slight activity on gramineous weeds which are commonly encountered noxious weeds, and are phytotoxic to broad-leafed plants which embrace many crops and cultivated trees, these chemicals only have limited application.

Diphenyl ethers represented by 2,4-dichloro-'-nitrodiphenyl ether have recently gained wide acceptance, but their selectivity in exterminating noxious weeds is insufficient.

The 4-phenoxy-phenoxyalkanecarboxylic acids recently proposed in West German Pat. Application No. p2223894/1972 exhibit some degree of improved selectivity, but suffer from the defect that their herbicidal activity is insufficient.

SUMMARY OF THE INVENTION

One object of the present invention is to provide α-[4-(5-mono-substituted or 3,5-di-substituted-pyridyl-2-oxy)phenoxy]alkanecarboxylic acids and derivatives thereof represented by the general formula (I):

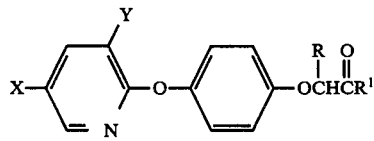

wherein X is a halogen atom; Y is a hydrogen atom, a halogen atom or a methyl group; R is a hydrogen atom or a straight or branched chain $(C_1-C_6)$alkyl group; and $R^1$ is a hydroxy group; a $(C_1-C_9)$alkoxy group in which the alkyl moiety thereof may be straight or branched chain and may be substituted with one or more of a halogen atom or a hydroxy group; an $-(OC_2H_4)_n-O-(C_1-C_4)$alkyl group in which the alkyl moiety thereof may be straight or branched chain and $n$ is an interger of from 1 to 5; a $(C_1-C_4)$alkylthio group in which the alkyl moiety thereof may be straight or branched chain; a $(C_2-C_4)$alkenyloxy group; a cyclohexyloxy group in which the cyclohexyl moiety thereof may be substituted with one or more of a halogen atom or a methyl group; a phenoxy group in which the aryl moiety thereof may be substituted with one or more of a halogen atom or a methyl group; a phenylthio group in which the aryl moiety thereof may be substituted with one or more of a halogen atom or a methyl group; a benzyloxy group in which the aryl moiety thereof may be substituted with one or more of a halogen atom or a methyl group; an amino group which may be substituted with one or more of a $(C_1-C_4)$alkyl group in which the alkyl moiety thereof may be straight or branched chain and may be substituted with a hydroxy group; a mono-$(C_1-C_4)$alkylamino group in which the alkyl moiety thereof may be straight or branched chain and is substituted with a $-COOR^4$ group in which $R^4$ is a hydrogen atom, a cation or a straight or branched chain $(C_1-C_4)$alkyl group; an anilino group in which the aryl moiety thereof may be substituted with one or more of a halogen atom or a methyl group; a benzylamino group; an amino group substituted with a heterocyclic group in which the heterocyclic moiety thereof may be substituted with one or more of a halogen atom or a methyl group; a morpholino group; a piperidino group; an $-OM$ group where M is a cation; or a halogen atom.

A further object of the present invention is to provide a herbicidal composition comprising a herbicidally effective amount of at least one compound of the above general formula (I) and one or more agriculturally acceptable adjuvants.

Still a further object of the invention is to provide a method for controlling weeds comprising applying a herbicidally effective amount of the above herbicidal composition to the weeds.

Yet another object of the invention is to provide a method of producing the compounds of the general formula (I) above.

DETAILED DESCRIPTION OF THE INVENTION

The compound of formula (I) of this invention which is useful as a herbicide (hereinafter, "herbicidal compound") contains a phenoxyalkanecarboxylic acid structure in the molecule, and from a chemical structural standpoint might appear to be similar to the known herbicidal compounds described hereinabove, i.e., phenoxyalkanecarboxylic acids (e.g., as disclosed in Japanese Patent Publication 5548/54). However, the herbicidal compound of formula (I) is a novel compound, and has unique herbicidal activity which differs from the herbicidal activities of known herbicidal compounds.

The herbicidal compound of this invention has the following two important characteristics.

(1) The compound of formula (I) has a strong selective herbicidal activity toward gramineous plants. On the other hand, since the compound affects broad-leafed plants to only a slight extent, especially those which have grown to some extent, it can be used with high safety on broad-leafed crops or cultivated trees. In other words, the compound of this invention has a reverse selectivity to, and a far higher selectivity, than known phenoxyalkanecarboxylic acids.

(2) The compound of formula (I) has high translocatability in the plant structure. The compound is absorbed by the foliage and roots of a plant, and primarily causes a decay of the meristematic cells in the nodes, which leads to withering, collapse and death of the plant. Accordingly, even when applied only to a very limited part of the plant structure, the compound exhibits a strong herbicidal activity, and weeds which have grown considerably wither and die due to the activity of the compound of this invention.

In the definitions with respect to formula (I) representing the herbicidal compound of this invention, suitable halogen atoms include bromine, chlorine, fluorine and iodine atoms, with chlorine atom being preferred, suitable straight or branched chain alkyl groups include methyl, ethyl, n-propyl, iso-propyl, n-butyl, iso-butyl, sec-butyl and tert-butyl groups, with a methyl group or an ethyl group being preferred, and suitable alkoxy groups are those containing as moieties the alkyl groups described above which may be straight or branched chain, with a methoxy group or an ethoxy group being preferred. The term "heterocyclic group" as used herein means groups such as a pyridyl group or a triazolyl group in which the pyridyl moiety or the triazolyl moiety thereof may be substituted with one or more of a halogen atom or a methyl group. The term "cation" for M means, for example, an alkali metal atoms such as sodium or potassium, an alkaline earth metal atom such as calcium or magnesium, or an ammonium group optionally substituted with a straight or branched chain ($C_1$-$C_4$)alkyl group, such as a methyl or ethyl group, or a straight or branched chain ($C_1$-$C_4$)alkyl group substituted with, for example, a hydroxy group.

Suitable examples of derivatives of the α-[4-(5-mono-substituted or 3,5-di-substituted-pyridyl-2-oxy)phenoxy]-alkanecarboxylic acid as set forth previously, other than the above, include an acid anhydride of the alkanecarboxylic acid, for example, α-[4-(3,5-dichloropyridyl-2-oxy)phenoxy]propionic anhydride, a polyester formed between the alkanecarboxylic acid and a polyol such as ethylene glycol, etc., for example, diethylene glycol di-{α-[4-(3,5-dichloropyridyl-2-oxy)-phenoxy]propionic acid} ester, and the like.

The herbicidal compound of the formula (I) can be used commercially as an active ingredient of herbicidal compositions, as will be seen from the Test Examples given hereinafter. Of the herbicidal compounds of the invention, those represented by the following formula (I'):

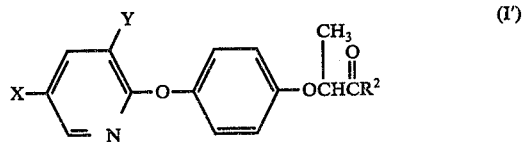

are preferred, and those represented by the following formula (I''):

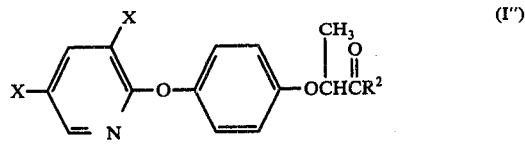

are further preferred, and those represented by the formula (I'''):

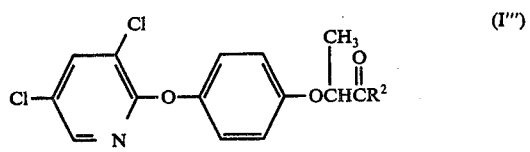

are especially preferred.

In the above formulae (I'), (I'') and (I'''), X is a halogen atom; Y is a hydrogen atom, a halogen atom or a methyl group; and $R^2$ is a hydroxy group, a ($C_1$-$C_9$)alkoxy group in which the alkyl moiety thereof may be straight or branched chain, an —(O$C_2H_4$)$_n$—O—($C_1$-$C_4$)alkyl group in which the alkyl moiety thereof may be straight or branched chain and $n$ is an integer of from 1 to 5, a ($C_1$-$C_4$)alkylthio group in which the alkyl moiety thereof may be straight or branched chain, a ($C_2$-$C_4$)alkenyloxy group, a cyclohexyloxy group in which the cyclohexyl moiety thereof may be substituted with one or more of a halogen atom or a methyl group, a benzyloxy group in which the aryl moiety thereof may be substituted with one or more of a halogen atom or a methyl group, an amino group which may be substituted with one or more of a straight or branched chain ($C_1$-$C_4$)alkyl group, an —NHCH$_2$COOR$^4$ group in which $R^4$ is a hydrogen atom, a cation or a straight or branched chain ($C_1$-$C_4$)alkyl group, an anilino group in which the aryl moiety thereof may be substituted with one or more of a halogen atom or a methyl group, an amino group substituted with a heterocyclic group, with a pyridyl group or a triazolyl group being preferred, in which the heterocyclic moiety thereof may be substituted with one or more of a halogen atom or a methyl group, a morpholino group, a piperidino group, or an —OM group, where M is a cation.

Typical examples of compounds of the formula (I) are given below.

| Compound No. | X | Y | R | R¹ | Melting Point (° C) | Boiling Point (° C) |
|---|---|---|---|---|---|---|
| 1 | Cl | H | CH₃ | OH | 103–104 | — |
| 2 | Br | H | CH₃ | OH | 135–139 | — |
| 3 | Cl | Cl | CH₃ | OH | 100–103 | — |
| 4 | Br | Br | CH₃ | OH | 68–70 | — |
| 5 | Cl | Cl | CH₃ | ONa | 104–110 | — |
| 6 | Cl | Cl | CH₃ | ONH₄ | — | — |
| 7 | Cl | Cl | CH₃ | ONH₂(CH₃)₂ | — | — |
| 8 | Br | Br | CH₃ | ONa | 45–50 | — |
| 9 | Cl | H | CH₃ | OCH₃ | 88–90 | — |
| 10 | Cl | H | CH₃ | OC₂H₅ | — | 165–166/3 mmHg |

-continued

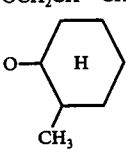

| Compound No. | X | Y | R | R¹ | Melting Point (°C) | Boiling Point (°C) |
|---|---|---|---|---|---|---|
| 11 | Cl | H | CH₃ | O-n-C₃H₇ | — | 175–178/3 mmHg |
| 12 | Cl | H | CH₃ | OCH₂CH=CH₂ | — | 205–207/5 mmHg |
| 13 | Cl | H | CH₃ | 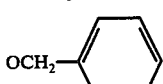 | — | 205–210/4 mmHg |
| 14 | Cl | H | CH₃ |  | — | 217–220/3 mmHg |
| 15 | Cl | H | CH₃ | SC₂H₅ | — | 185–187/3 mmHg |
| 16 | Cl | H | CH₃ | 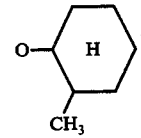 | — | 230–235/4 mmHg |
| 17 | Cl | H | C₂H₅ | OCH₃ | — | 165–170/3 mmHg |
| 18 | Cl | H | C₂H₅ | OC₂H₅ | — | 189–190/3 mmHg |
| 19 | Cl | H | n-C₄H₉ | OCH₃ | — | 165–167/4 mmHg |
| 20 | Br | H | CH₃ | OCH₃ | — | 198–200/2 mmHg |
| 21 | Br | H | C₂H₅ | OC₂H₅ | — | 202–205/1 mmHg |
| 22 | I | H | CH₃ | OCH₃ | — | 221–224/1 mmHg |
| 23 | I | H | CH₃ | OC₂H₅ | — | 199–203/1.5 mmHg |
| 24 | Cl | Cl | CH₃ | OCH₃ | 82–84 | 189–193/3 mmHg |
| 25 | Cl | Cl | CH₃ | OC₂H₅ | — | 191–193/3 mmHg |
| 26 | Cl | Cl | CH₃ | O-n-C₃H₇ | — | 201–203/2 mmHg |
| 27 | Cl | Cl | CH₃ | O-i-C₃H₇ | — | 198–200/2 mmHg |
| 28 | Cl | Cl | CH₃ | O-n-C₄H₉ | — | 215–217/2 mmHg |
| 29 | Cl | Cl | CH₃ | O-sec-C₄H₉ | — | 220–221/2 mmHg |
| 30 | Cl | Cl | CH₃ | O-i-C₄H₉ | — | 212–214/2 mmHg |
| 31 | Cl | Cl | CH₃ | OCH₂CH=CH₂ | — | 205–208/2 mmHg |
| 32 | Cl | Cl | CH₃ | O-n-C₅H₁₁ | — | 222–225/2 mmHg |
| 33 | Cl | Cl | CH₃ | 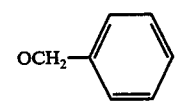 | — | 222–223/2 mmHg |
| 34 | Cl | Cl | CH₃ | 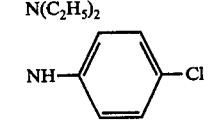 | — | 215–216/2 mmHg |
| 35 | Cl | Cl | CH₃ | OC₂H₄O-n-C₄H₉ | — | 168–170/4 mmHg |
| 36 | Cl | Cl | CH₃ | SC₂H₅ | — | 208–210/2 mmHg |
| 37 | Cl | Cl | C₂H₅ | OC₂H₅ | — | 205–208/3 mmHg |
| 38 | Cl | Cl | n-C₆H₁₃ | OC₂H₅ | — | 239–241/3 mmHg |
| 39 | Br | Br | CH₃ | OCH₃ | — | 215–220/1 mmHg |
| 40 | Br | Br | CH₃ | OC₂H₅ | — | 225–226/2 mmHg |
| 41 | Br | Br | CH₃ | O-n-C₄H₉ | — | 228–230/2 mmHg |
| 42 | Br | Br | CH₃ | O-n-C₅H₁₁ | — | 242–245/2 mmHg |
| 43 | Br | Br | CH₃ | OC₂H₄O-n-C₄H₉ | — | 249–250/2 mmHg |
| 44 | Br | Br | C₂H₅ | OCH₃ | — | 223–225/2 mmHg |
| 45 | Br | Br | n-C₃H₇ | OCH₃ | — | 220–221/2 mmHg |
| 46 | Br | Br | i-C₃H₇ | OCH₃ | — | 198–200/2 mmHg |
| 47 | Br | Br | n-C₆H₁₃ | OC₂H₅ | — | 242–244/2 mmHg |
| 48 | I | I | CH₃ | OCH₃ | — | — |
| 49 | I | I | CH₃ | OC₂H₅ | 85–87 | — |
| 50 | Cl | Br | CH₃ | OCH₃ | — | 201–204/2 mmHg |
| 51 | Br | Cl | CH₃ | OC₂H₅ | — | 205–208/2 mmHg |
| 52 | Cl | CH₃ | CH₃ | OCH₃ | — | 190–198/1 mmHg |
| 53 | Cl | H | CH₃ | N(C₂H₅)₂ | — | 164/5 mmHg |
| 54 | Cl | H | CH₃ | 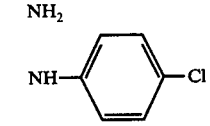 | — | 195–200/3 mmHg |
| 55 | Cl | Cl | CH₃ | NH₂ | 168–170 | — |
| 56 | Cl | Cl | CH₃ | 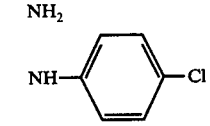 | 172–175 | — |

-continued

| Compound No. | X | Y | R | R¹ | Melting Point (°C) | Boiling Point (°C) |
|---|---|---|---|---|---|---|
| 57 | Cl | Cl | CH₃ | NH—<triazole> | 148–150 | — |
| 58 | Cl | Cl | CH₃ | NH—<pyridyl> | — | 255–260/2 mmHg |
| 59 | Br | Br | CH₃ | NH—<pyridyl> | — | 245–250/2 mmHg |
| 60 | Cl | H | CH₃ | Cl | — | — |
| 61 | Cl | Cl | CH₃ | Cl | — | — |
| 62 | Br | Br | CH₃ | Cl | — | — |
| 63 | Cl | Cl | CH₃ | OC₂H₄Cl | — | — |
| 64 | Cl | Cl | CH₃ | OC₂H₄OH | — | — |
| 65 | Cl | Cl | CH₃ | NHC₂H₄OH | 86–89 | — |
| 66 | Cl | Cl | CH₃ | N(C₂H₄OH)₂ | — | — |
| 67 | Cl | Cl | CH₃ | NHCH₂COOH | 132–137 | — |
| 68 | Cl | Cl | CH₃ | NHCH₂COOC₂H₅ | 110.5–112 | — |
| 69 | Cl | Cl | CH₃ | NHCH₂COONa | — | — |
| 70 | Cl | Cl | CH₃ | —N(morpholino) | 115–118 | — |
| 71 | Cl | Cl | CH₃ | —N(piperidino) | — | — |
| 72 | Cl | Cl | CH₃ | ONH₂(C₂H₄OH)₂ | — | — |
| 73 | Cl | Cl | CH₃ | NHCH₂—C₆H₅ | — | — |
| 74 | Cl | Cl | CH₃ | (OC₂H₄)₃OCH₃ | — | — |
| 75 | Cl | H | H | OH | 143–147 | — |
| 76 | Cl | H | H | OC₂H₅ | 62–64 | — |
| 77 | Cl | H | H | O-n-C₄H₉ | — | 195/3 mmHg |
| 78 | Br | H | H | OH | 130—132 | — |
| 79 | Br | H | H | OCH₃ | — | 205–207/1 mmHg |
| 80 | Cl | Cl | H | OH | 178–180 | — |
| 81 | Cl | Cl | H | OCH₃ | 52–54 | — |
| 82 | Br | Br | H | OH | 242–245 | — |
| 83 | Br | Br | H | OCH₃ | — | 235–238/2 mmHg |
| 84 | Br | Br | H | O-n-C₄H₉ | — | 220–222/2 mmHg |
| 85 | Cl | Cl | CH₃ | OCH₂CH(CH₂)₃CH₃<br>│<br>C₂H₅ | — | — |

Other than the above-described compounds, an aldehyde, thioamide or amidine of α-[4-(3,5-dichloropyridyl-2-oxy)-phenoxy]propionic acid, and a hydrochloric acid addition salt at the N-position of α-[4-(5-chloropyridyl-2-oxy)phenoxy]-propionic acid have also sufficient herbicidal effects.

The herbicidal compound of this invention of the formula (I) can be prepared by the following method.

A substituted pyridine of the formula (II):

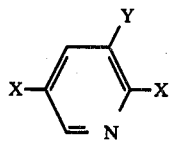

(II)

wherein X and Y are the same as defined hereinbefore, and a substituted phenol of the formula (III):

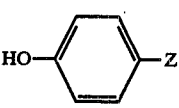

(III)

wherein Z is a hydroxy group, a (C₁–C₅)alkoxy group in which the alkyl moiety thereof may be straight or branched chain, or an

group wherein R is the same as defined hereinbefore and $R^3$ is a hydroxy group, a $(C_1-C_9)$alkoxy group in which the alkyl moiety thereof may be straight or branched chain, or an amino group, are first condensed, e.g., using an equimolar amount of the compound of the formula (II) and the compound of the formula (III), in the presence of an alkaline material in an amount of about 1 to 1.2 molar times the amount of the compound of formula (III) to form a substituted pyridyl phenyl ether of the formula (IV):

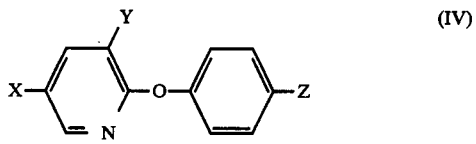
(IV)

wherein X, Y and Z are the same as defined hereinbefore.
When Z is an

$-OCHCR^3$ group, an object compound of the formula (V):

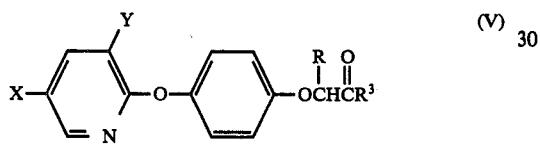
(V)

wherein X, Y, R and $R^3$ are the same as defined hereinbefore, is obtained. If desired, the resulting product of the formula (V) can be treated by a conventional method to convert $R^3$ to $R^1$ to thereby form the herbicidal compound of the formula (I).

When Z is a $(C_1-C_5)$alkoxy group or a hydroxy group, the resulting substituted pyridyl-p-hydroxyphenyl ether of the formula (VI):

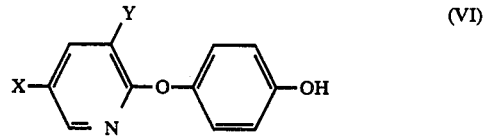
(VI)

wherein X and Y are the same as defined hereinbefore, and an α-haloalkanecarboxylic acid or a derivative thereof of the formula (VII):

(VII)

wherein X, R and $R^3$ are the same as defined hereinbefore, are then condensed, e.g., using an equimolar amount of the compound of formula (VI) and the compound of the formula (VII), in the presence of an alkaline material in an amount of about 1 to 1.2 molar times the compound of the formula (VI), with or without prior dealkylation (i.e., to remove the alkyl moiety of the $(C_1-C_5)$alkoxy group), to form an object compound of the formula (V) as described above.

The above method for the production of the compounds of formula (I) or intermediates used therein will now be described in greater detail.

(1) A method for preparing a compound of the formula (V):

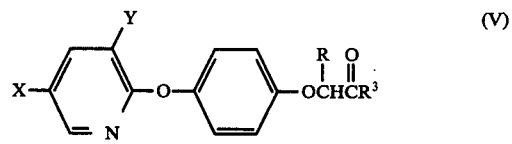
(V)

wherein X, Y, R and $R^3$ are the same as defined above, comprising condensing a substituted pyridine of the formula (II):

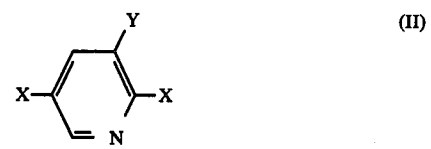
(II)

wherein X and Y are the same as defined above, with a p-hydroxyphenoxyalkanecarboxylic acid or a derivative thereof of the formula (VIII):

(VIII)

wherein R and $R^3$ are the same as defined above, the compound of formula (II) being used in an amount of about equimolar of the compound of formula (VIII), in the presence of an alkaline material in an amount of about 1 to 1.2 molar times the compound of the formula (VIII) at a temperature of at least about 50° C., preferably 70° to 150° C., at a pressure of preferably atmospheric pressure for about 1 to 20 hours, preferably 1 to 10 hours.

(2) A method for preparing a compound of the formula (V):

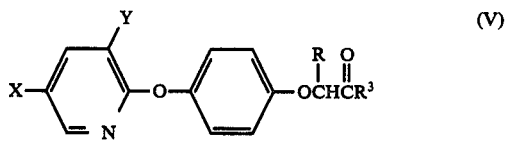
(V)

wherein X, Y, R and $R^3$ are the same as defined above, comprising condensing a substituted pyridine of the fomrula (II):

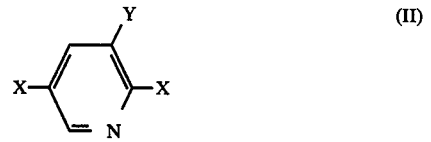
(II)

wherein X and Y are the same as defined above, with hydroquinone, the compound of formula (II) being used in an amount of about equimolar of hydroquinone, in the presence of an alkaline material in an amount of about 1 to 1.2 molar times the hydroquinone, at a temperature of at least about 50° C., preferably 70° to 150°

C., at a pressure of preferably atmospheric pressure for about 1 to 20 hours to form a substituted pyridyl-p-hydroxyphenyl ether of the formula (VI):

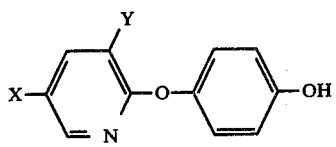
(VI)

wherein X and Y are the same as defined above, and then condensing the compound of the formula (VI) with an α-haloalkanecarboxylic acid or a derivative thereof of the formula (VII):

(VII)

wherein X, R and R³ are the same as defined above, the compound of formula (VI) being used in an amount of about equimolar of the compound of formula (VII), in the presence of an alkaline material in an amount of about 1 to 1.2 molar times the compound of the formula (VI), at a temperature of about 40° to 120° C. at a pressure of preferably atmospheric pressure for about 0.5 to 10 hours.

(3) A method for preparing a compound of the formula (V):

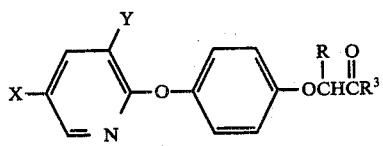
(V)

wherein X, Y, R and R³ are the same as defined above, comprising condensing a substituted pyridine of the formula (II):

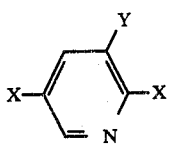
(II)

wherein X and Y are the same as defined above, with a hydroquinone monoalkyl ether of the formula (IX):

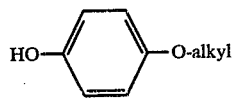
(IX)

wherein "alkyl" represents a straight or branched chain (C₁ - C₅) alkyl group, the compound of formula (II) being used in an amount of about equimolar of the compound of the formula (IX), in the presence of an alkaline material in an amount of about 1 to 1.2 molar times the compound of formula (IX), at a temperature of at least about 50° C., preferably 70° to 150° C., at a pressure of preferably atmospheric pressure for about 1 to 20 hours, preferably 1 to 10 hours, to form a substituted pyridyl-p-alkoxyphenyl ether of the formula (X):

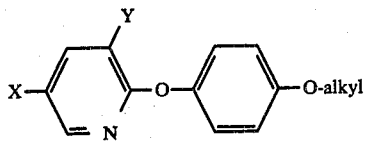
(X)

wherein X, Y and "alkyl" are the same as defined above, dealkylating the compound of the formula (X) to form a substituted pyridyl-p-hydroxyphenyl ether: (VI):

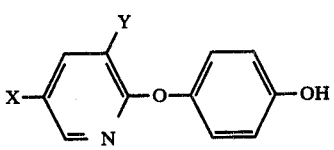
(VI)

wherein X and Y are the same as defined above, and then condensing the compound of the formula (VI) with an α-haloalkanecarboxylic acid or a derivative thereof of the formula (VII):

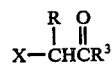
(VII)

wherein X, R and R³ are the same as defined above, the compound of formula (VI) being used in an amount of about equimolar of the compound of formula (VII), in the presence of an alkaline material in an amount of about 1 to 1.2 molar times the compound of formula (VI), at a temperature of about 40° to 120° C. at a pressure of preferably atmospheric pressure for about 0.5 to 10 hours.

(4) An α-[4-(5-mono-substituted or 3,5-di-substituted-pyridyl2-oxy)phenoxy]alkanecarboxylic acid of the formula (Va):

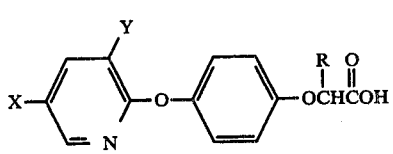
(Va)

wherein X, Y and R are the same as defined above, (the compound of the formula (V) in which R³ is a hydroxy group) is reacted with:
  (a) an alkaline material (e.g., sodium hydroxide, potassium hydroxide, ammonia, etc.) to form a salt;
  (b) an alcohol (e.g., a (C₁ - C₉) alcohol such as methyl alcohol, ethyl alcohol, isopropyl alcohol, etc.) to form an ester;
  (c) an amine (e.g., a mono- or di-(C₁ - C₄)alkylamine such as methylamine, diethylamine, etc.) to form an amide; or
  (d) a halogenating agent (e.g., SOCl₂, PCl₃, PCl₅, POCl₃, etc.) to form a halide.

(5) An α-[4-(5-mono-substituted or 3,5-di-substituted-pyridy-12-oxy)phenoxy]alkanecarboxylic acid easter of the formula (Vb):

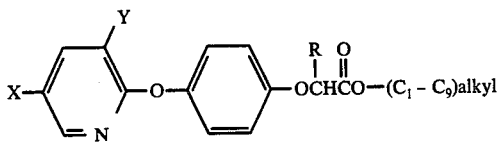

(Vb)

wherein X, Y and R are the same as defined above, (the compound of the formula (V) in which $R^3$ is a ($C_1$-$C_9$)alkoxy group), or the ester obtained by Method (4)-(b) above, (a) is subjected to an ester-interchange reaction (e.g., using an alcohol as described in Method (4)-(b) above) in the presence of a Lewis acid catalyst (such as $BF_3$, etc.) to form another ester;

(b) is reacted with an amide (e.g., an amine as described in Method (4)-(c) above) to form an amine;

(c) is hydrolyzed (e.g., with an acid or alkali) to form an acid.

(6) An α-[4-(5-mono-substituted or 3,5-di-substituted-pyridyl2-oxy)phenoxy]alkanecarbonyl halide of the formula (Vc):

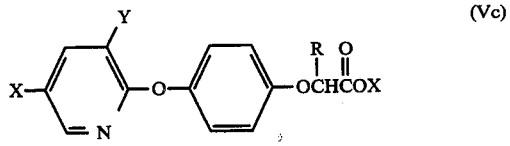

(Vc)

wherein X, Y and R are the same as defined above, obtained by Method (4)-(d) above is reacted with:

(a) an alcohol (e.g., an alcohol as described in Method (4)-(b) above) to form an ester;

(b) an amine (e.g., an amine as described in Method (4)-(c) above) to form an amide.

Methods (4) to (6) are conventional methods and are described in, for example, Romeo B. Wagner and Harry D. Zook, Synthetic Organic Chemistry, pp. 411 – 589, John Wiley & Sons INc., New York, London.

Examples of suitable alkaline materials which can be used in all of the condensation reactions described above are alkali metal hydroxides such as sodium hydroxide or potassium hydroxide, and alkali metal carbonates such as sodium carbonate or potassium carbonate. In the first condensation, a suitable reaction temperature is at least about 50° C., preferably 70° to 150° C., and the reaction time is generally about 1 to 20 hours, preferably 1 to 10 hours. A ketone such as methyl ethyl ketone or methyl isobutyl ketone, or an aprotic-polar solvent, such as dimethylformamide, dimethylcetamide, dimethyl sulfoxide, N-methylpyrrolidone, hexamethylphosphoramide or sulfolane, can be used in this reaction as a solvent. In the second condensations, a suitable reaction temperature is about 40° to 120° C., and the reaction time is generally about 0.5 to 10 hours. In this second condensation, a ketone such as methyl ethyl ketone or methyl isobutyl ketone can be used as a solvent.

In the dealkylation, the dealkylating agent is used in an amount of about 1.5 to 2.0 molar times the compound of formula (X).

When pyridine hydrochloride is used as a dealkylating agent in the dealkylation, the reaction temperature is desirably about 50° to 250° C., more desirably about 150° to 200° C., the pressure is preferably atmospheric pressure, and the reaction time is most generally about 1 to 10 hours. When a hydrohalic acid having a concentration of about 40 to 60% such as hydrobromic acid or hydroiodic acid is used as a dealkylating agent, the dealkylating reaction is desirably carried out in the presence of a lower fatty acid solvent, such as acetic acid or acetic anhydride, in an amount of about 1 to 50 times the volume of the compound of the formula (X) for about 1 to 10 hours at a pressure of preferably atmospheric pressure at a temperature of about the boiling point of the solvent.

Some specific examples of preparing the herbicidal compounds of this invention are shown below. Unless otherwise indicated herein, all parts, percents, ratios and the like are by weight.

PREPARATION EXAMPLE 1

Preparation of Methyl α[4-(5-Chloropyridyl-2-oxy)-phenoxy]-propionate:

Into 100 ml of methyl ethyl ketone were suspended 33.2 g of 4-(5-chloropyridyl-2-oxy)phenol, 30.1 g of methyl α-bromopropionate and 50.0 g of potassium carbonate, and reaction conducted stirring for 1 hour at reflux temperature (80° to 85° C.). The reaction product was poured into water and then extracted with chloroform. After washing the extract with a 2–3% sodium hydroxide aqueous solution and water, the chloroform was evaporated off using an aspirator to give 43.5 g (yield: 95%) of the final product having a melting point of 88° to 90° C.

PREPARATION EXAMPLE 2

Preparation of α-[4-(5-Chloropyridyl-2-oxy)phenoxy]-propionic Acid:

39.5 g of methyl α-[4-(5-chloropyridyl-2-oxy)phenoxy]-propionate as obtained in Preparation Example 1, 30 ml of a 45% sodium hydroxide aqueous solution and 300 ml of methanol were mixed and reacted for 1 hour at reflux temperature (i.e., 50°–250° C.). After allowing the reaction product to cool, the excess of the methanol was evaporated off using an aspirator, and water was added to the resulting residue, which was subsequently made acidic with a 5% sulfuric acid aqueous solution. The precipitate thus-formed was filtered and dried to give 34 g (yield: 87%) of the final product having a melting point of 103° to 104° C.

PREPARATION EXAMPLE 3

Preparation of 2-Methylcyclohexyl-α-[4-(5-Chloropyridyl-2-oxy)-phenoxy]propionate:

To 3.1 g of α-[4-(5-chloropyridyl-2-oxy)phenoxyl]-propionyl chloride were added 1.4 g of 2-methylcyclohexanol, 1.0 g of pyridine and 20 ml of benzene, and the system reacted with stirring on a water bath at 50° C. for 1 hour. The reaction product was poured into water. The benzene was then separated from the water and evaporated off using an aspirator. Subsequent distillation at reduced pressure gave the final product having a boiling point of 205° to 210° C./4 mmHg.

PREPARATION EXAMPLE 4

Preparation of Methyl α-[4-(3,5-Dichloropyridyl-2-oxy)phenoxyl]-propionate:

(A) Into 200 ml of methyl ethyl ketone were suspended 51.2 g of 4-(3,5-dichloropyridyl-2-oxy)phenol, 41 g of methyl α-bromopropionate and 66 g of potassium carbonate. The resulting suspension was reacted with stirring for 2 hours at reflux temperature (80° to 85° C.). The reaction product was poured into water and extracted with chloroform. After washing the extract with a 2-3% sodium hydroxide aqueous solution and water, the chloroform was evaporated off using an aspirator to give 55 g (yield: 81%) of the final product having a boiling point of 189° to 193° C./3 mmHg and a melting point of 82° to 84° C.

(B) To a mixture of 4.6 g of 3,5-dichloro-2-bromopyridine, 4.7 g of methyl α-(4-hydroxyphenoxy)-propionate and 3.3 g of potassium carbonate was added 10 ml of methyl ethyl ketone, and the system reacted with stirring for about 6 hours as the reflux temperature (80° to 85° C.). The reaction product was poured into a suitable amount of water and extracted with chloroform. The extract was washed with water and dried over anhydrous sodium sulfate. After drying, the chloroform was evaporated off using an aspirator. Subsequent distillation at reduced pressure gave 5.4 g of the final product.

PREPARATION EXAMPLE 5

Preparation of Sodium α-[4-(3,5-Dichloropyridyl-2-oxy)phenoxy]-propionate:

Into 10 ml of water were suspended 6.6 g of α-[4-(3,5-dichloropyridyl-2-oxy)phenoxy]propionic acid and 0.8 g of sodium hydroxide, and the system reacted by heating at 90° to 100° C. for 2 hours. The water was removed from the reaction product at reduced pressure followed by drying in a vacuum desiccator to give 6.8 g (yield: 97%) of the powdery final product having a melting point of 104° to 110° C.

PREPARATION EXAMPLE 6

Preparation of Methyl 4-(3,5-Dichloropyridyl-2-oxy)-phenoxy Acetate:

Into 20 ml of methyl ethyl ketone were added 9 g of 4-(3,5-dichloropyridyl-2-oxy)phenol, 6.4 g of methyl bromoacetate and 11.6 g of potassium carbonate and the system reacted with stirring at 75° to 80° C. for about 3 hours. The reaction product was poured into water and extracted with chloroform. After washing the extract with a 2-3% sodium hydroxide aqueous solution and water, the chloroform was evaporated off using an aspirator to give 11.7 g (yield: 80%) of the final product having a melting point of 52° to 54° C.

The herbicidal compound of this invention can be dispersed in water to produce an aqueous dispersion. The herbicidal compound can also be formulated into various forms such as an emulsifiable concentrate, wettable powder, watermiscible solution, dust or granules by optionally incorporating conventional agriculturally acceptable adjuvants, for example, a carrier such as diatomaceous earth, calcium hydroxide, calcium carbonate, talc, white carbon, kaolin, bentonite, or Jeeklite (trade name for a zeolite, produced by Jeeklite Co.), solvents such as n-hexane, toluene, xylene, solvent naphtha, ethanol, dioxane, acetone, isophorone, methyl isobutyl ketone, dimethylformamide, dimethyl sulfoxide or water, or an anionic or nonionic surface active agent such as a sodium alkylsulfate, a sodium alkylbenzenesulfonate, sodium ligninsulfonate, a polyoxyethylene lauryl ether, a polyoxyethylene alkylaryl ether, a polyoxyethylene fatty acid ester, or a polyoxyethylene sorbitan fatty acid ester. A suitable ratio of the compound of this invention to the adjuvant(s) ranges from about 1-90:99-10 by weight, preferably 1-70:99-30 by weight.

The herbicidal composition of this invention can also be mixed or used together with suitable agricultural chemicals such as other herbicides, insecticides or fungicides, or mixed with an agricultural agent such as a fertilizer or soil conditioner or soil or sand, at the time of formulation or application. Sometimes, such joint usage brings about improved effects.

Typical examples of herbicidal formulations containing a compound of this invention are shown below.

FORMULATION EXAMPLE 1

40 parts by weight of methyl α-[4-(5-chloropyridyl-2-oxy)phenoxyl]propionate, 47 parts by weight of Jeeklite, 8 parts by weight of white carbon, 2 parts by weight of Lavelin S (trade name for a sodium naphthalenesulfonate-formaldehyde condensate produced by Daiichi Kogyo Seiyaku Co., Ltd.), as a surface active agent, and 3 parts by weight of Sorpol 5039 (trade name for a sulfate of a polyoxyethylene alkylaryl ether produced by Toho Chemical Co., Ltd.), as a surface active agent, were uniformly mixed to form a wettable powder.

FORMULATION EXAMPLE 2

10 parts by weight of N,N-diethyl α-[4-(5-chloropyridyl-2-oxy)phenoxy]propionamide, 80 parts by weight of xylene, 3 parts by weight of a calcium alkylbenzenesulfonate, as a surface active agent, and 7 parts by weight of a polyoxyethylene sorbitan fatty acid ester, as a surface active agent, were uniformly mixed to form an emulsifiable concentrate.

FORMULATION EXAMPLE 3

20 parts by weight of 2-methyl cyclohexyl α-[4-(5-chloropyridyl-2-oxy)phenoxy]propionate, 79 parts by weight of bentonite, and 1 part by weight of Monogen (trade name for a sodium higher alcohol sulfate produced by Daiichi Kogyo Seiyaku Co., Ltd.) in the form of powder were mixed and pulverized to form a dust.

FORMULATION EXAMPLE 4

44.2 parts by weight of methyl α-[4-(3,5-dichloropyridyl-2-oxy)phenoxyl]propionate, 42.8 parts by weight of Jeeklite, 8 parts by weight of white carbon, 3 parts by weight of Sorpol 5050 (trade name for a dialkylsulfosuccinate produced by Toho Chemical Co., Ltd.), as a surface active agent, and 2 parts by weight of Laveline S, as a surface active agent, were uniformly mixed to form a wettable powder.

FORMULATION EXAMPLE 5

85 parts by weight of sodium α-[4-(3,5-dichloropyridyl-2-oxy)phenoxy]propionate, 5 parts by weight of white carbon, and 10 parts by weight of a sodium alkylbenzenesulfonate, as a surface active agent, were uniformly mixed to form a wettable powder.

FORMULATION EXAMPLE 6

10 parts by weight of n-butyl α-[4-(3,5-dichloropyridyl-2-oxy)phenoxy]propionate, 80 parts by weight of methyl ethyl ketone, 7 parts by weight of Noigen EA 150 (trade name for a polyoxyethylene glycol alkylphenyl ether produced by Daiichi Kogyo Seiyaku Co., Ltd.), as a surface active agent, and 3 parts by weight of Hitenol No. 8 (trade name for an ammonium ether-sulfate produced by Daiichi Kogyo Seiyaku Co., Ltd.), as a surface active agent, were uniformly mixed to form an emulsifiable concentrate.

FORMULATION EXAMPLE 7

10 parts by weight of methyl 4-(3,5-dichloropyridyl-2-oxy)phenoxy acetate, 80 parts by weight of xylene, 3 parts by weight of a calcium alkylbenzenesulfonate, as a surface active agent, and 7 parts by weight of a polyoxyethylene sorbitan fatty acid ester, as a surface active agent, were uniformly mixed to form an emulsifiable concentrate.

The unique herbicidal activity of the herbicidal compound of this invention has been briefly described hereinabove, and will now be described in greater detail below.

(1) The compound of this invention can be used to kill gramineous weeds by pre-emergence soil treatment or foliar treatment during the growth of weeds. In particular, the compound of this invention can be used to kill gramineous weeds which have grown to a height of about 1 meter by a foliar treatment. Since the compound of this invention is extremely safe for use on broad-leafed agricultural crops such as soybeans, peanuts and cotton plants, the compound is suitable for selective weed control in upland farms.

(2) If the method of application, the dosage, and the time of application are appropriately selected, for example, if the weeds which are growing together with a plant such as corn, etc., are subjected to a foliar treatment with a small amount (5–20 g/a) of the active ingredient of this invention after the plant has grown to some degree, the compound of this invention can be applied to farms where gramineous crops are cultivated. Furthermore, when the dosage of the compound is excessively increased or the compound is used together with other herbicides, the composition can be used to kill weeds other than gramineous weeds.

(3) The compound of this invention has low toxicity to fish, and does not affect fisheries.

The herbicidal compound of this invention is most suitably applied to upland farms, especially upland farms where broad-leafed crops are cultivated, and can also be applied to orchards, forests and various non-agricultural lands. The compound of this invention can be applied as a soil treatment or a foliar treatment in upland farm conditions or under flooded conditions. A suitable rate of application varies according to various factors such as the climatic conditions, the soil conditions, the form of the chemical, the time of application, the method of application, or the types of cultivated crops to which it is applied and the main weeds to be controlled. When the compound of this invention is used in the form of a solid preparation (e.g., dust or granules), the amount of the active ingredient is 0.1 to 1,000 g per are (100 m²), preferably 1 to 700 g, and more preferably 5 to 300 g, per are.

The herbicidal activity testing of the compound of this invention and the results obtained are shown below.

TEST EXAMPLE 1

Each 1/3,000 are (1/30 m²) flat was charged with soil to provide upland conditions. Predetermined amounts of seeds of edible barnyard grass, radish and soybeans were sown and covered with soil containing seeds of large crab-grass and barnyard grass as gramineous weeds and polygonums, chickweeds and bog stichworts as broad-leafed weeds, to a thickness of about 1 cm. Three days after sowing, an aqueous dispersion of each of the herbicidal compounds shown in Table 1 (the formulae thereof are set out in an earlier part of this specification) below was sprayed thereon, and the growth of the weeds was visually evaluated 20 days after the spraying. The results obtained are shown in Table 1. The degree of growth inhibition shown in Table 1 was evaluated on a scale of 10 grades in which 10 indicates that growth was completely inhibited and 1 indicates no inhibition.

TABLE 1

| Compound No. | Amount of Active Ingredient (g/are) | Edible Barnyard Grass | Radish | Soybeans | Gramineous Weeds | Broadleafed Weeds |
|---|---|---|---|---|---|---|
| 1 | 100 | 10 | 1 | 1 | 10 | 1 |
|   | 50  | 10 | 1 | 1 | 10 | 1 |
| 2 | 100 | 10 | 1 | 1 | 10 | 1 |
|   | 50  | 10 | 1 | 1 | 10 | 1 |
| 3 | 100 | 10 | 1 | 1 | 10 | 1 |
|   | 50  | 10 | 1 | 1 | 10 | 1 |
| 4 | 100 | 10 | 1 | 1 | 10 | 1 |
|   | 50  | 10 | 1 | 1 | 10 | 1 |
| 5 | 100 | 10 | 1 | 1 | 10 | 1 |
|   | 50  | 10 | 1 | 1 | 10 | 1 |
| 6 | 100 | 10 | 1 | 1 | 10 | 1 |
|   | 50  | 10 | 1 | 1 | 10 | 1 |
| 7 | 100 | 10 | 1 | 1 | 10 | 1 |
|   | 50  | 10 | 1 | 1 | 10 | 1 |
| 8 | 100 | 10 | 1 | 1 | 10 | 1 |
|   | 50  | 10 | 1 | 1 | 10 | 1 |
| 9 | 100 | 10 | 1 | 1 | 10 | 1 |
|   | 50  | 10 | 1 | 1 | 10 | 1 |
| 10 | 100 | 10 | 1 | 1 | 10 | 1 |
|    | 50  | 10 | 1 | 1 | 10 | 1 |
| 11 | 100 | 10 | 1 | 1 | 10 | 1 |
|    | 50  | 10 | 1 | 1 | 10 | 1 |
| 12 | 100 | 10 | 1 | 1 | 10 | 1 |
|    | 50  | 10 | 1 | 1 | 10 | 1 |
| 13 | 100 | 10 | 1 | 1 | 10 | 1 |
|    | 50  | 10 | 1 | 1 | 10 | 1 |
| 14 | 100 | 10 | 1 | 1 | 10 | 1 |
|    | 50  | 10 | 1 | 1 | 10 | 1 |
| 15 | 100 | 10 | 1 | 1 | 10 | 1 |
|    | 50  | 9  | 1 | 1 | 9  | 1 |
| 16 | 100 | 10 | 1 | 1 | 10 | 1 |
|    | 50  | 10 | 1 | 1 | 10 | 1 |
| 18 | 100 | 8  | 1 | 1 | 9  | 1 |
|    | 50  | 6  | 1 | 1 | 7  | 1 |
| 20 | 100 | 10 | 1 | 1 | 10 | 1 |
|    | 50  | 10 | 1 | 1 | 10 | 1 |
| 21 | 100 | 10 | 1 | 1 | 10 | 1 |
|    | 50  | 10 | 1 | 1 | 10 | 1 |
| 22 | 100 | 10 | 1 | 1 | 10 | 1 |
|    | 50  | 10 | 1 | 1 | 10 | 1 |
| 23 | 100 | 10 | 1 | 1 | 10 | 1 |
|    | 50  | 10 | 1 | 1 | 10 | 1 |
| 24 | 100 | 10 | 1 | 1 | 10 | 1 |
|    | 50  | 10 | 1 | 1 | 10 | 1 |
| 25 | 100 | 10 | 1 | 1 | 10 | 1 |
|    | 50  | 10 | 1 | 1 | 10 | 1 |
| 26 | 100 | 10 | 1 | 1 | 10 | 1 |
|    | 50  | 10 | 1 | 1 | 10 | 1 |
| 27 | 100 | 10 | 1 | 1 | 10 | 1 |
|    | 50  | 10 | 1 | 1 | 10 | 1 |
| 28 | 100 | 10 | 1 | 1 | 10 | 1 |
|    | 50  | 10 | 1 | 1 | 10 | 1 |
| 29 | 100 | 10 | 1 | 1 | 10 | 1 |
|    | 50  | 10 | 1 | 1 | 10 | 1 |
| 30 | 100 | 10 | 1 | 1 | 10 | 1 |
|    | 50  | 10 | 1 | 1 | 10 | 1 |
| 31 | 100 | 10 | 1 | 1 | 10 | 1 |
|    | 50  | 10 | 1 | 1 | 10 | 1 |
| 32 | 100 | 10 | 1 | 1 | 10 | 1 |
|    | 50  | 10 | 1 | 1 | 10 | 1 |
| 33 | 100 | 10 | 1 | 1 | 10 | 1 |
|    | 50  | 10 | 1 | 1 | 10 | 1 |
| 34 | 100 | 10 | 1 | 1 | 10 | 1 |
|    | 50  | 10 | 1 | 1 | 10 | 1 |
| 35 | 100 | 10 | 1 | 1 | 10 | 1 |
|    | 50  | 10 | 1 | 1 | 10 | 1 |
| 36 | 100 | 10 | 1 | 1 | 10 | 1 |
|    | 50  | 10 | 1 | 1 | 10 | 1 |
| 37 | 100 | 10 | 1 | 1 | 10 | 1 |
|    | 50  | 10 | 1 | 1 | 10 | 1 |
| 39 | 100 | 10 | 1 | 1 | 10 | 1 |
|    | 50  | 10 | 1 | 1 | 10 | 1 |
| 40 | 100 | 10 | 1 | 1 | 10 | 1 |
|    | 50  | 10 | 1 | 1 | 10 | 1 |
| 41 | 100 | 10 | 1 | 1 | 10 | 1 |
|    | 50  | 10 | 1 | 1 | 10 | 1 |
| 42 | 100 | 10 | 1 | 1 | 10 | 1 |
|    | 50  | 10 | 1 | 1 | 10 | 1 |

TABLE 1-continued

| Compound No. | Amount of Active Ingredient (g/are) | Degree of Growth Inhibition | | | | |
|---|---|---|---|---|---|---|
| | | Edible Barnyard Grass | Radish | Soybeans | Gramineous Weeds | Broadleafed Weeds |
| 43 | 100 | 10 | 1 | 1 | 10 | 1 |
| | 50 | 10 | 1 | 1 | 10 | 1 |
| 44 | 100 | 10 | 1 | 1 | 10 | 1 |
| | 50 | 10 | 1 | 1 | 10 | 1 |
| 47 | 100 | 10 | 1 | 1 | 10 | 1 |
| | 50 | 9 | 1 | 1 | 10 | 1 |
| 48 | 100 | 10 | 1 | 1 | 10 | 1 |
| | 50 | 10 | 1 | 1 | 10 | 1 |
| 49 | 100 | 9 | 1 | 1 | 10 | 1 |
| | 50 | 8 | 1 | 1 | 10 | 1 |
| 50 | 100 | 10 | 1 | 1 | 10 | 1 |
| | 50 | 10 | 1 | 1 | 10 | 1 |
| 51 | 100 | 10 | 1 | 1 | 10 | 1 |
| | 50 | 10 | 1 | 1 | 10 | 1 |
| 52 | 100 | 10 | 1 | 1 | 10 | 1 |
| | 50 | 10 | 1 | 1 | 10 | 1 |
| 53 | 100 | 10 | 1 | 1 | 10 | 1 |
| | 50 | 10 | 1 | 1 | 10 | 1 |
| 54 | 100 | 10 | 1 | 1 | 10 | 1 |
| | 50 | 10 | 1 | 1 | 10 | 1 |
| 55 | 100 | 10 | 1 | 1 | 10 | 1 |
| | 50 | 10 | 1 | 1 | 10 | 1 |
| 56 | 100 | 10 | 1 | 1 | 10 | 1 |
| | 50 | 10 | 1 | 1 | 10 | 1 |
| 57 | 100 | 10 | 1 | 1 | 10 | 1 |
| | 50 | 10 | 1 | 1 | 10 | 1 |
| 58 | 100 | 10 | 1 | 1 | 10 | 1 |
| | 50 | 10 | 1 | 1 | 10 | 1 |
| 59 | 100 | 10 | 1 | 1 | 10 | 1 |
| | 50 | 10 | 1 | 1 | 10 | 1 |
| 60 | 100 | 10 | 1 | 1 | 10 | 1 |
| | 50 | 10 | 1 | 1 | 10 | 1 |
| 61 | 100 | 10 | 1 | 1 | 10 | 1 |
| | 50 | 10 | 1 | 1 | 10 | 1 |
| 62 | 100 | 10 | 1 | 1 | 10 | 1 |
| | 50 | 10 | 1 | 1 | 10 | 1 |
| 65 | 100 | 10 | 1 | 1 | 10 | 1 |
| | 50 | 10 | 1 | 1 | 10 | 1 |
| 68 | 100 | 10 | 1 | 1 | 10 | 1 |
| | 50 | 10 | 1 | 1 | 10 | 1 |
| 70 | 100 | 10 | 1 | 1 | 10 | 1 |
| | 50 | 10 | 1 | 1 | 10 | 1 |
| 75 | 100 | 10 | 1 | 1 | 10 | 1 |
| | 50 | 9 | 1 | 1 | 10 | 1 |
| 76 | 100 | 9 | 1 | 1 | 10 | 1 |
| | 50 | 6 | 1 | 1 | 9 | 1 |
| 77 | 100 | 8 | 1 | 1 | 10 | 1 |
| | 50 | 7 | 1 | 1 | 9 | 1 |
| 78 | 100 | 10 | 1 | 1 | 10 | 1 |
| | 50 | 10 | 1 | 1 | 10 | 1 |
| 79 | 100 | 10 | 1 | 1 | 10 | 1 |
| | 50 | 10 | 1 | 1 | 10 | 1 |
| 80 | 100 | 10 | 1 | 1 | 10 | 1 |
| | 50 | 10 | 1 | 1 | 10 | 1 |
| 81 | 100 | 10 | 1 | 1 | 10 | 1 |
| | 50 | 10 | 1 | 1 | 10 | 1 |
| 82 | 100 | 10 | 1 | 1 | 10 | 1 |
| | 50 | 10 | 1 | 1 | 10 | 1 |
| 83 | 100 | 10 | 1 | 1 | 10 | 1 |
| | 50 | 10 | 1 | 1 | 10 | 1 |
| 84 | 100 | 10 | 1 | 1 | 10 | 1 |
| | 50 | 10 | 1 | 1 | 10 | 1 |

TEST EXAMPLE 2

Each 1/10,000 are (1/100 m²) pot was charged with soil to provide upland conditions, and predetermined amounts of seeds of edible barnyard grass and soybeans were sown and covered with soil to a thickness of about 1 cm. When the edible barnyard grass reached the two-leaf stage, an aqueous dispersion of each of the herbicidal compounds shown in Table 2 below was applied to the foliage in a predetermined amount. Twenty days after the treatment with the chemical, the growth of the barnyard grass and soybeans was visually evaluated, and the degree of growth inhibition was evaluated on the same scale as in Test Example 1. The results obtained are shown in Table 2 below.

TABLE 2

| Compound No. | Amount of Active Ingredient (ppm) | Degree of Growth Inhibition | |
|---|---|---|---|
| | | Edible Barnyard Grass | Soybeans |
| 1 | 2,000 | 10 | 1 |
| | 1,000 | 10 | 1 |
| 2 | 2,000 | 10 | 1 |
| | 1,000 | 10 | 1 |
| 3 | 2,000 | 10 | 1 |
| | 1,000 | 10 | 1 |
| 4 | 2,000 | 10 | 1 |
| | 1,000 | 10 | 1 |
| 5 | 2,000 | 10 | 1 |
| | 1,000 | 10 | 1 |
| 6 | 2,000 | 10 | 1 |
| | 1,000 | 10 | 1 |
| 7 | 2,000 | 10 | 1 |
| | 1,000 | 10 | 1 |
| 8 | 2,000 | 10 | 1 |
| | 1,000 | 10 | 1 |
| 9 | 2,000 | 10 | 1 |
| | 1,000 | 10 | 1 |
| 10 | 2,000 | 10 | 1 |
| | 1,000 | 10 | 1 |
| 11 | 2,000 | 10 | 1 |
| | 1,000 | 10 | 1 |
| 12 | 2,000 | 10 | 1 |
| | 1,000 | 10 | 1 |
| 13 | 2,000 | 10 | 1 |
| | 1,000 | 10 | 1 |
| 14 | 2,000 | 10 | 1 |
| | 1,000 | 10 | 1 |
| 15 | 2,000 | 10 | 2 |
| | 1,000 | 9 | 2 |
| 16 | 2,000 | 10 | 3 |
| | 1,000 | 10 | 1 |
| 17 | 2,000 | 7 | 1 |
| | 1,000 | 7 | 1 |
| 18 | 2,000 | 10 | 2 |
| | 1,000 | 10 | 1 |
| 19 | 2,000 | 6 | 1 |
| | 1,000 | 5 | 1 |
| 20 | 2,000 | 10 | 1 |
| | 1,000 | 10 | 1 |
| 22 | 2,000 | 10 | 1 |
| | 1,000 | 10 | 1 |
| 23 | 2,000 | 10 | 1 |
| | 1,000 | 10 | 1 |
| 24 | 2,000 | 10 | 1 |
| | 1,000 | 10 | 1 |
| 25 | 2,000 | 10 | 1 |
| | 1,000 | 10 | 1 |
| 26 | 2,000 | 10 | 1 |
| | 1,000 | 10 | 1 |
| 27 | 2,000 | 10 | 1 |
| | 1,000 | 10 | 1 |
| 28 | 2,000 | 10 | 1 |
| | 1,000 | 10 | 1 |
| 29 | 2,000 | 10 | 1 |
| | 1,000 | 10 | 1 |
| 30 | 2,000 | 10 | 1 |
| | 1,000 | 10 | 1 |
| 31 | 2,000 | 10 | 1 |
| | 1,000 | 10 | 1 |
| 32 | 2,000 | 10 | 1 |
| | 1,000 | 10 | 1 |
| 35 | 2,000 | 10 | 1 |
| | 1,000 | 10 | 1 |
| 36 | 2,000 | 10 | 1 |
| | 1,000 | 10 | 1 |
| 37 | 2,000 | 10 | 1 |
| | 1,000 | 10 | 1 |
| 39 | 2,000 | 10 | 1 |
| | 1,000 | 10 | 1 |
| 40 | 2,000 | 10 | 1 |
| | 1,000 | 10 | 1 |
| 41 | 2,000 | 10 | 1 |
| | 1,000 | 10 | 1 |
| 42 | 2,000 | 10 | 1 |
| | 1,000 | 10 | 1 |
| 43 | 2,000 | 10 | 1 |
| | 1,000 | 10 | 1 |
| 48 | 2,000 | 10 | 1 |
| | 1,000 | 10 | 1 |
| 49 | 2,000 | 10 | 1 |
| | 1,000 | 10 | 1 |
| 50 | 2,000 | 10 | 1 |
| | 1,000 | 10 | 1 |
| 51 | 2,000 | 10 | 1 |
| | 1,000 | 10 | 1 |
| 52 | 2,000 | 10 | 1 |
| | 1,000 | 10 | 1 |

TABLE 2-continued

| Compound No. | Amount of Active Ingredient (ppm) | Degree of Growth Inhibition Edible Barnyard Grass | Soybeans |
|---|---|---|---|
| 53 | 2,000 | 10 | 2 |
|  | 1,000 | 10 | 1 |
| 54 | 2,000 | 10 | 1 |
|  | 1,000 | 10 | 1 |
| 55 | 2,000 | 10 | 1 |
|  | 1,000 | 10 | 1 |
| 57 | 2,000 | 10 | 1 |
|  | 1,000 | 10 | 1 |
| 58 | 2,000 | 10 | 1 |
|  | 1,000 | 10 | 1 |
| 59 | 2,000 | 10 | 1 |
|  | 1,000 | 10 | 1 |
| 60 | 2,000 | 10 | 1 |
|  | 1,000 | 10 | 1 |
| 61 | 2,000 | 10 | 1 |
|  | 1,000 | 10 | 1 |
| 62 | 2,000 | 10 | 1 |
|  | 1,000 | 10 | 1 |
| 65 | 2,000 | 10 | 1 |
|  | 1,000 | 10 | 1 |
| 68 | 2,000 | 10 | 1 |
|  | 1,000 | 10 | 1 |
| 70 | 2,000 | 10 | 1 |
|  | 1,000 | 7 | 1 |
| 78 | 2,000 | 10 | 1 |
|  | 1,000 | 8 | 1 |
| 79 | 2,000 | 10 | 1 |
|  | 1,000 | 9 | 1 |
| 80 | 2,000 | 10 | 1 |
|  | 1,000 | 10 | 1 |
| 81 | 2,000 | 10 | 1 |
|  | 1,000 | 10 | 1 |
| 82 | 2,000 | 10 | 1 |
|  | 1,000 | 5 | 1 |
| 83 | 2,000 | 10 | 1 |
|  | 1,000 | 8 | 1 |
| 84 | 2,000 | 10 | 1 |
|  | 1,000 | 10 | 1 |
| Comparison: 2,4-Dichlorophenoxy Acetic Acid Dimethylamine Salt | 2,000 | 3 | 10 |
|  | 1,000 | 2 | 10 |

TEST EXAMPLE 3

Each 1/900 are (1/9 m²) pot was charged with soil to provide upland conditions. A predetermined amount of seeds of each of the crops shown in Table 3 below was sown in the pot and covered with soil containing seeds of various weeds, as shown in Table 3 below, to a thickness of about 2 cm. At the stage of emergence, an aqueous dispersion of each of the herbicidal compounds shown in Table 3 below was sprayed thereon. Twenty days after the spraying, the growth of the crops and the weeds were visually evaluated and the degree of growth inhibition was shown on the same scale as in Test Example 1. The results obtained are shown in Table 3 below.

TABLE 3

| Compound No. | Amount of Active Ingredient (g/are) | Soybeans | Red Beans | Peanuts | Corn | Cotton | Sunflower | Flax | Beet | Lettuce | Eggplant | Green Onions |
|---|---|---|---|---|---|---|---|---|---|---|---|---|
| 1 | 20 | 1 | 1 | 1 | 10 | 1 | 1 | 1 | 1 | 1 | 1 | 1 |
|  | 5 | 1 | 1 | 1 | 10 | 1 | 1 | 1 | 1 | 1 | 1 | 1 |
| 5 | 20 | 1 | 1 | 1 | 10 | 1 | 1 | 1 | 1 | 1 | 1 | 1 |
|  | 5 | 1 | 1 | 1 | 10 | 1 | 1 | 1 | 1 | 1 | 1 | 1 |
| 9 | 20 | 1 | 1 | 1 | 10 | 1 | 1 | 1 | 1 | 1 | 1 | 1 |
|  | 5 | 1 | 1 | 1 | 10 | 1 | 1 | 1 | 1 | 1 | 1 | 1 |
| 24 | 20 | 1 | 1 | 1 | 10 | 1 | 1 | 1 | 1 | 1 | 1 | 1 |
|  | 5 | 1 | 1 | 1 | 10 | 1 | 1 | 1 | 1 | 1 | 1 | 1 |

| Compound No. | Amount of Active Ingredient (g/are) | Spinach | Cabbage | Radish | Tomatoes | Carrots | Burdock | Cucumber | Edible Barnyard Grass | Large Crabglass | Barnyard Grass |
|---|---|---|---|---|---|---|---|---|---|---|---|
| 1 | 20 | 1 | 1 | 1 | 1 | 1 | 1 | 1 | 10 | 10 | 10 |
|  | 5 | 1 | 1 | 1 | 1 | 1 | 1 | 1 | 9 | 9 | 9 |
| 5 | 20 | 1 | 1 | 1 | 1 | 1 | 1 | 1 | 10 | 10 | 10 |
|  | 5 | 1 | 1 | 1 | 1 | 1 | 1 | 1 | 10 | 10 | 10 |
| 9 | 20 | 1 | 1 | 1 | 1 | 1 | 1 | 1 | 10 | 10 | 10 |
|  | 5 | 1 | 1 | 1 | 1 | 1 | 1 | 1 | 10 | 10 | 9 |
| 24 | 20 | 1 | 1 | 1 | 1 | 1 | 1 | 1 | 10 | 10 | 10 |
|  | 5 | 1 | 1 | 1 | 1 | 1 | 1 | 1 | 10 | 10 | 10 |

TEST EXAMPLE 4

Each 1/1,000 are (1/10 m²) pot was charged with soil to provide upland conditions. Predetermined amounts of seeds of italian rye grass (Lotium italicum Brann.) and edible barnyard grass were sown and lightly covered with soil. When the italian rye grass and edible barnyard grass grew to a height of 25 to 30 cm (four-leaf stage), an aqueous dispersion of each of the herbicidal compounds shown in Table 4 below was applied to the foliage in a predetermined amount. Thirty days after treatment with the chemical, the growth of the italian rye grass and edible barnyard grass was visually evaluated, and the degree of growth inhibition was evaluated on the same scale as in Test Example 1. The results obtained are shown in Table 4 below.

TABLE 4

| Compound No. | Amount of Active Ingredient (ppm) | Italian Rye Grass | Edible Barnyard Grass |
|---|---|---|---|
| 3 | 100 | 10 | 10 |
|  | 50 | 10 | 10 |
| 4 | 100 | 10 | 10 |
|  | 50 | 10 | 10 |
| 5 | 100 | 10 | 10 |
|  | 50 | 10 | 10 |
| 20 | 100 | 10 | 10 |
|  | 50 | 10 | 10 |
| 22 | 100 | 10 | 10 |
|  | 50 | 10 | 10 |
| 23 | 100 | 10 | 10 |
|  | 50 | 10 | 10 |
| 24 | 100 | 10 | 10 |
|  | 50 | 10 | 10 |
| 25 | 100 | 10 | 10 |
|  | 50 | 10 | 10 |
| 26 | 100 | 10 | 10 |
|  | 50 | 10 | 10 |
| 28 | 100 | 10 | 10 |
|  | 50 | 10 | 10 |
| 31 | 100 | 10 | 10 |
|  | 50 | 10 | 10 |

TABLE 4-continued

| Compound No. | Amount of Active Ingredient (ppm) | Degree of Growth Inhibition | |
|---|---|---|---|
| | | Italian Rye Grass | Edible Barnyard Grass |
| 32 | 100 | 10 | 10 |
| | 50 | 10 | 10 |
| 35 | 100 | 10 | 10 |
| | 50 | 10 | 10 |
| 36 | 100 | 10 | 10 |
| | 50 | 10 | 10 |
| 40 | 100 | 10 | 10 |
| | 50 | 10 | 10 |
| 41 | 100 | 10 | 10 |
| | 50 | 10 | 10 |
| 42 | 100 | 10 | 10 |
| | 50 | 10 | 10 |

TEST EXAMPLE 5

Each 1/10,000 are (1/100 m$^2$) pot was charged with soil and completely saturated with water. A predetermined amount of air-dried seeds of barnyard grass was sown and lightly covered with soil. When the barnyard grass germinated above the ground, water was put into the pot to a depth of 3 cm to provide flooded conditions, and an aqueous dispersion of each of the herbicidal compounds shown in Table 5 was poured into the pot. Twenty days after treatment with the dispersion, the surviving barnyard grass in the pot was pulled out, dried in air, and weighed. The percentage of the amount of surviving weeds based on the untreated pot was calculated, and the degree of growth determined. The results obtained are shown in Table 5.

TABLE 5

| Compound No. | Degree of Growth (%) Amount of Active Ingredient (g/are) | | |
|---|---|---|---|
| | 40 | 20 | 10 |
| 1 | 0 | 0 | 0 |
| 9 | 0 | 0 | 0 |
| 10 | 0 | 0 | 0 |
| 60 | 0 | 0 | 0 |

TEST EXAMPLE 6

In a field for cotton and peanuts, an area of about 50 m$^2$ was used as one test area, and the testing was carried out using varying amounts of each of the herbicidal compounds shown in Table 6 below. In each test area, the crops were grown for 60 days after sowing. Gramineous weeds such as large crabglass, barnyard grass and green foxtail as the primary weeds had grown to a height of 20 to 30 cm. Broadleafed weeds such as pale smartweed and beggar-ticks were also growing.

50 g, 100 g or 150 g of a 10% emulsifiable concentrate in accordance with the formulation in Formulation Example 2 above was diluted with 5 liters of water, and each composition was sprayed onto the plants from above. In the area to which the composition containing the compound of the present invention had been applied, decay of the weeds near the ground and the nodular parts thereof was observed about 7 days after spraying, and the weeds began to drop and entirely turn yellow. On the 15th day, all of the weeds had withered and died. However, no phytotoxicity to the cotton and peanut plants was observed. The results obtained are shown in Table 6. The evaluation grades in Table 6 are on the same scale as in Test Example 1.

TABLE 6

| Compound No. | Amount of Active Ingredient (g/are) | Degree of Growth Inhibition | | | | | | |
|---|---|---|---|---|---|---|---|---|
| | | Cotton | Peanuts | Large Crabgrass | Barnyard Grass | Green Foxtail | Pale Smartweed | Beggar-ticks |
| 24 (Invention) | 30 | 1 | 1 | 10 | 10 | 10 | 1 | 1 |
| | 20 | 1 | 1 | 10 | 10 | 10 | 1 | 1 |
| | 10 | 1 | 1 | 10 | 10 | 10 | 1 | 1 |
| Ethyl α-[4-(4-Chlorophenoxy)-phenoxy]propionate (Comparison) | 30 | 1 | 1 | 8 | 7 | 8 | 1 | 1 |
| | 20 | 1 | 1 | 6 | 7 | 7 | 1 | 1 |
| | 10 | 1 | 1 | 3 | 4 | 4 | 1 | 1 |

While the invention has been described in detail and with reference to specific embodiments thereof, it will be apparent to one skilled in the art that various changes and modifications can be made therein without departing from the spirit and scope thereof.

What is claimed is:

1. A compound having the formula:

$$\begin{array}{c} Y \\ X-\underset{N}{\underset{\parallel}{\bigcirc}}-O-\bigcirc-O-\underset{H}{\overset{CH_3}{\underset{|}{C}}}-\overset{O}{\overset{\parallel}{C}}-R \end{array}$$

where X is a halogen atom, Y is a hydrogen atom, a halogen atom or a methyl group, and R is a (C$_1$-C$_4$) alkylthio group in which the alkyl moiety thereof may be straight or branched chain, or a phenylthio group in which the aryl moiety thereof may be substituted with one or more of a halogen atom or a methyl group.

2. The compound of claim 1, wherein X is a chlorine atom, Y is a hydrogen atom or a chlorine atom, and R is a (C$_1$-C$_4$) alkylthio group or a phenylthio group in which the aryl moiety thereof may be substituted with a chlorine atom.

3. The compound of claim 2, wherein said compound is α-[4-(5-chloropyridyl-2-oxy) phenoxy] propionic acid ethylthioester.

4. The compound of claim 2, wherein said compound is α-[4-(3,5-dichloropyridyl-2-oxy) phenoxy] propionic acid ethylthioester.

5. The compound of claim 2, wherein said compound is α-[4-(5-chloropyridyl-2-oxy) phenoxy] propionic acid o-chlorophenylthioester.

6. A herbicidal composition comprising a herbicidally effective amount of the compound as defined in claim 1 as an active ingredient and an agriculturally acceptable adjuvant.

7. A method for controlling noxious weeds in the presence of cultivated crops, which comprises applying a herbicidally effective amount of the herbicidal composition as defined in claim 6 to an upland area where the cultivated crops are growing.

8. A method for selectively controlling gramineous weeds in the presence of broad-leafed crops, which comprises applying a herbicidally effective amount of the herbicidal composition as defined in claim 6 to an upland ara where the broad-leafed crops are growing, thereby to kill gramineous weeds selectively by withering.

* * * * *